(12) United States Patent
Kirschner

(10) Patent No.: US 6,451,585 B1
(45) Date of Patent: Sep. 17, 2002

(54) PRODUCT FOR PRE-EMPTIVE POTENTIAL IN REMEDIATION OF OIL SPILLS

(76) Inventor: Leon Kirschner, 7650 Lavergne, Skokie, IL (US) 60076

( * ) Notice: Subject to any disclaimer, the term of this patent is extended or adjusted under 35 U.S.C. 154(b) by 64 days.

(21) Appl. No.: 09/595,382

(22) Filed: Jun. 15, 2000

Related U.S. Application Data

(63) Continuation of application No. 09/105,387, filed on Jun. 26, 1998, now Pat. No. 6,121,038.

(51) Int. Cl.⁷ .............................................. C12S 13/00
(52) U.S. Cl. .................... 435/262; 435/177; 435/262.5; 435/264
(58) Field of Search ............................... 435/262, 262.5, 435/264, 281, 174, 177, 179, 180, 182; 210/610, 611, 616; 71/64.11; 424/93.3–93.51

(56) References Cited

U.S. PATENT DOCUMENTS

| | | | | |
|---|---|---|---|---|
| 3,843,517 A | * | 10/1974 | McKinney et al. | 210/11 |
| 3,860,490 A | * | 1/1975 | Guttag | 435/182 |
| 4,042,495 A | * | 8/1977 | Marconi et al. | 210/610 |
| 4,087,356 A | * | 5/1978 | Marconi et al. | 210/610 |
| 4,415,661 A | * | 11/1983 | Thirumalachar et al. | 435/174 |
| 4,415,662 A | * | 11/1983 | Thirumalachar et al. | 435/176 |
| 5,244,574 A | * | 9/1993 | Gatt et al. | 210/610 |
| 5,275,943 A | * | 1/1994 | Dituro | 435/179 |
| 5,340,376 A | * | 8/1994 | Cunningham | 71/6 |
| 5,348,803 A | * | 9/1994 | Schlaemus et al. | 428/402.2 |
| 5,401,413 A | * | 3/1995 | Gatt et al. | 210/610 |
| 5,443,845 A | * | 8/1995 | Felix | 424/490 |
| 5,510,112 A | * | 4/1996 | Gatt et al. | 424/450 |
| 5,575,998 A | * | 11/1996 | Nemec et al. | 424/93.3 |
| 5,807,724 A | * | 9/1998 | Resnick | 435/177 |
| 6,121,038 A | * | 9/2000 | Kirschner | 435/262.5 |

* cited by examiner

Primary Examiner—William H. Beisner
(74) Attorney, Agent, or Firm—Martin Faier; Faier & Faier, P.C.

(57) ABSTRACT

A process for pre-emptive potential in bioremediation of oil spills comprising the steps of fabricating cells of micro-organisms capable of degrading hydrocarbons, encapsulating the cells into pods dissolvable in a non-hydrocarbon environment such as water, introducing the pods into a body of petroleum contained in a vessel which if unintentionally fractured to release the body of petroleum into the non-hydrocarbon environment will also release the cells, causing the cells to open and allow the micro-organism to degrade the hydrocarbon and consume the oil spill. The process may also include the step of recovering pods which are not released into the non-hydrocarbon environment from the body of petroleum. The invention also includes a product for pre-emptive bioremediation of oil spills which has cells of micro-organisms capable of degrading hydrocarbons encapsuled in pods and which can be introduced into a body of petroleum during transport and storage and which are activated to degrade hydrocarbon and consume petroleum released into a non-hydrocarbon environment, wherein the pods also contain means for removing unactivated micro-organism cells from the body of petroleum.

18 Claims, 4 Drawing Sheets

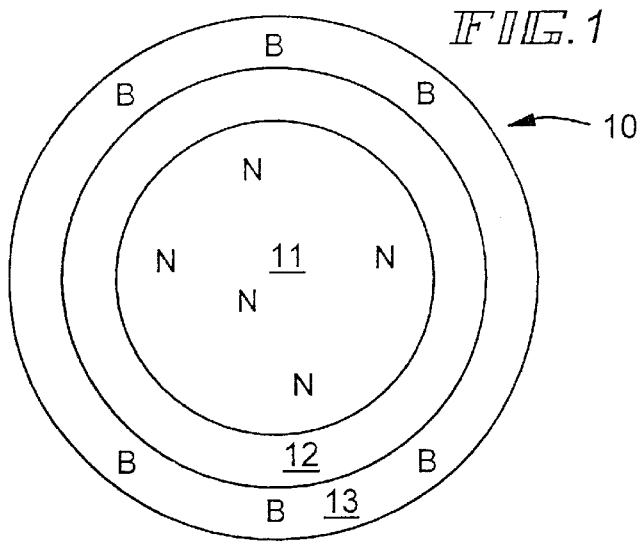
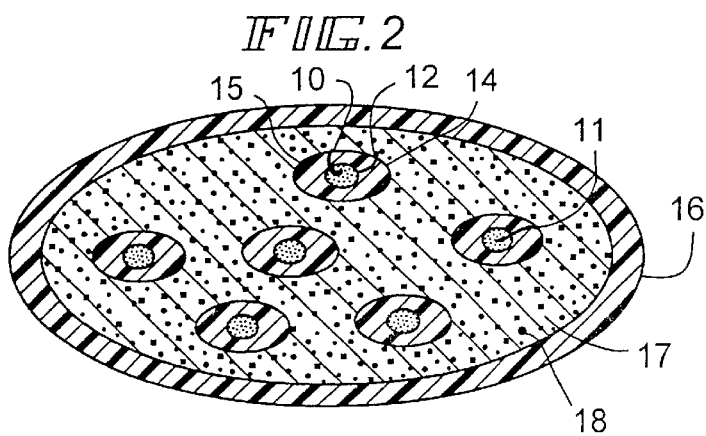
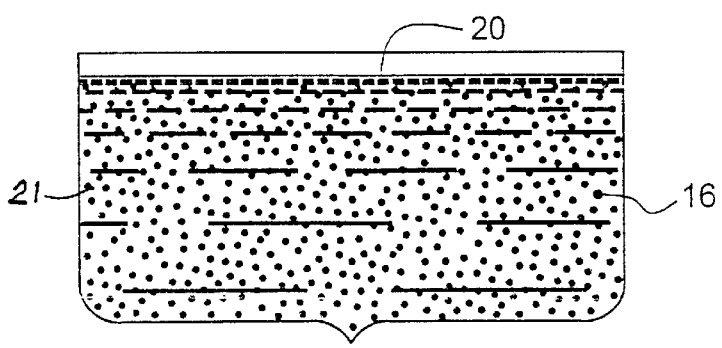

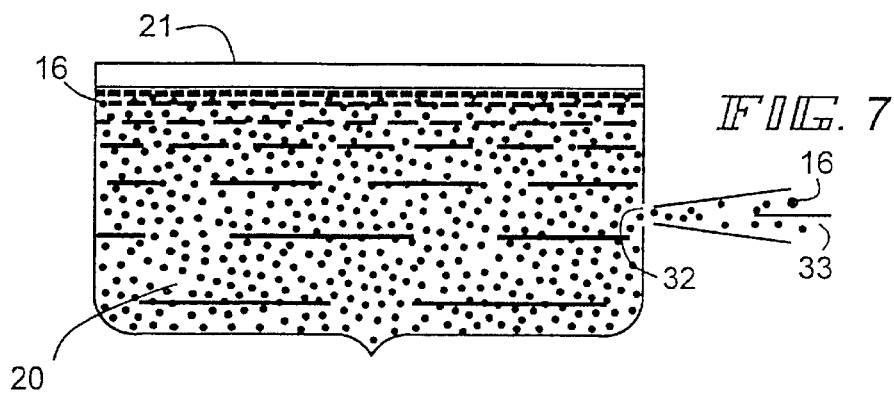
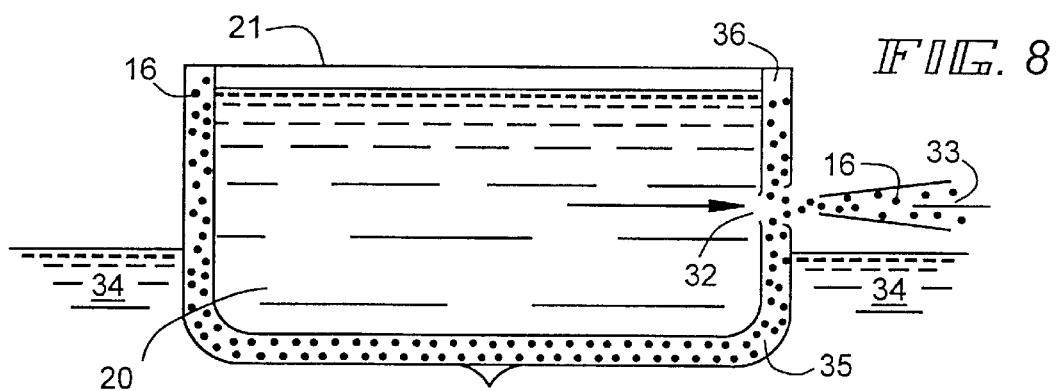
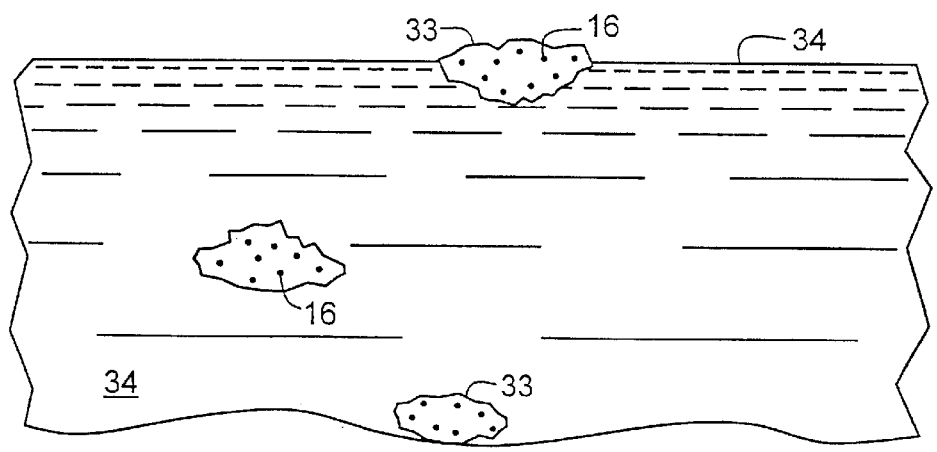

PRODUCT FOR PRE-EMPTIVE POTENTIAL IN REMEDIATION OF OIL SPILLS

This is a continuation of application Ser. No. 09/105,387 now U.S. Pat. No 6,121,038 filed on Jun. 26, 1998.

BACKGROUND AND SUMMARY OF THE INVENTION

This invention relates to a product and method for pre-emptive potential in remediation of oil spills. The invention is more particularly concerned with methods for both installing such a product into a body of petroleum at the wellhead source, in a pipeline or a cargo hold or storage tank, or at some other step as desired during the process of bringing the petroleum from its source to market, before a spill occurs, and recovering said product if a spill does not occur. The product embodying the present invention consists of a novel capsule, coated pellet, (The term "pellet" herein also refers to spheres, irrespective of the various techniques utilized to produce said pellet or sphere, or capsule) or pod, any of which may incorporate a time releasant formulation and which also contain micro-organisms capable of consuming hydrocarbon materials, which micro-organisms are released when the capsule or pellet is exposed to an aqueous environment. The product may also contain magnetic or para-magnetic or other materials which may affect the density of the capsule or pellet and also provide for its recoverability.

1. The Field of Invention

Oil spills have become disastrous to the environment. Such spills are generally treated through physical containment of the spilled oil and removal, using mechanical techniques, such as containment rings and vacuum removal systems. Other means for treating such spills include direct application to the spill of dispersants and application of bioremediation agents, such as aerobic micro-organisms, enzymes and nutrients. These methodologies have been used with varying degrees of effectiveness, depending upon many variables, such as the size and depth of the spill, as well as its location and accessibility, the speed with which it develops and travels, the configuration of the spill, whether the spill is at the surface or submerged in the water, the environmental risk to land and sea life, including wildlife, the turbulence of the waters containing the spill, as well as many other factors and considerations. Limited success in adequately dealing with such spills evidences the need for a product and method for dealing with an oil spill promptly, irrespective of its location, configuration and accessibility, with minimum disruption to the environment, in an economical manner, and through use of a universal system which is not dependent upon the variables of the spill.

2. Description of the Prior Art

The concept of bioremediation of oil spills is well known in the prior art. For example, Gatt et al teaches treating oil spills with dispersants by applying liposomes to water for forming a monomolecular layer of phospholipid molecules which break up layers of oil into droplets taught in U.S. Pat. No. 5,244,574, and to enhance biodegradation of organic wastes by increasing the availability for enhanced bacterial interaction as disclosed in U.S. Pat. No. 5,401,413. Gatt et al in U.S. Pat. No. 5,510,112 also suggests a composition for enhancing such biodegradation of organic wastes.

In U.S. Pat. Nos. 4,415,661 and 4,415,662 Thurumalachar et al suggests degradation of land or seaborne spills by use of microorganisms or enzymes, or with the use of carriers or detergents, without deleterious effect. Guttag et al in U.S. Pat. No. 3,860,490 teaches a process of subjecting micro-organism susceptible material to a microorganism, with controlled time or quick release bioremediating agents. Cunningham U.S. Pat. No. 5,340,376 discloses controlled release microbe nutrients and a method for bioremediation through the use of such enhanced organisms. DiTuro (in U.S. Pat. No. 5,275,943) and Felix (in U.S. Pat. No. 5,443,845) have provided timed-release coated tablets and the like for biological degradation of organic material which dissolve over time when placed in an aqueous environment.

Other prior art patents of interest pertinent to the subject of this application are McKinney et al U.S. Pat. No. 3,843,517, Marconi et al U.S. Pat. Nos. 4,042,495 and 4,087,356, and Schlaemus et al U.S. Pat. No. 5,348,803.

These patents relate to the treatment of oil spills with dispersants and microorganisms, as contained in oil insoluble and water soluble capsule or pellet forms. Such dispersants are usually intended to keep the dispersant on the surface of the oil spill, and all of them deal with materials which are applied after the spill occurs. None have any means for recovery of the materials capable of treating an oil spill but which have not actually been called into use for that purpose.

SUMMARY OF THE INVENTION

This invention adds pre-emption, reclamation and reuse, not taught by the prior art. Additionally, the invention uses anaerobic micro-organisms (such as vibrio desulfuricants) for remediation of submerged petroleum products, which anaerobes result in an overall exponential increase in speed of remediation, and also adds versatility to the art of remediation as applied to the inadvertent release of petroleum products into an aqueous environment during transport or storage, or to an intentional release of oil products, which also requires remediation.

The use of such anaerobic micro-organisms offers bioremediation to those petroleum products which sink below the surface of the water, and often to the floor of the sea, where known application techniques for remediation do not reach submerged oil spills.

Pre-emption is achieved by incorporating within the petroleum products, before a spill occurs, remediating agents contained in capsules, coated pellets, or pods having cores of varying densities. Such agents are inert and inactive when encapsulated or within the coated pellets, but are activated when not in the encapsulated environment. These encapsulated or pelletized agents are preferably dispersed throughout a body of petroleum. The capsules or pellets may be installed into the petroleum (The terms "petroleum", "petroleum product", and "petroleum mass" are synonymous with one another unless otherwise indicated) at the wellhead or in a pipeline, in a cargo hold, at a refinery or at any desired location during the processing and transport or storage of the petroleum product.

Preferably, these capsules or pellets are reclaimable when not activated and may be reused. Such reclamation may be accomplished through magnetic (utilizing either ferromagnetic, diamagnetic or paramagnetic materials, or a combination of some or all of them) separation, centrifugation, filtration, electrostatic or ionic precipitation, vaporization, or heat or vacuum distillation or a combination of such techniques. The capsules or pellets may be constructed to permit ease of reclamation and reuse.

Capsules or pellets with a core containing micro-organisms, surrounded by time dissolvable layers of nutrients and other enhancements, may be compounded using prior art skills and formulations. Such capsules, pellets, or pods of varying sizes and/or densities, so as to embody the present invention, may also be novelly compounded to include iron or other compound [within either the capsule, pellet, or pod core and/or their surrounding (encapsulating) material or coating (pellet)], so as to permit the capsules, pellets, or pods to be varied in density, preferably to approximate the density of the petroleum product in which they are placed, and to encourage their removal from a body of petroleum by the techniques described above, when desired. The capsule, pellet or pod may also be sprayed with an aqueous soluble electrostatically charged material, or marked with material having magnetic, electrostatic, or electro-conductive properties. The core or encapsulating material or coating may also be either fabricated with gas bubbles, or contain evacuated or gas filled glass beads (bubbles or beads of varying sizes), so as to affect the density of the capsule or pellet. These capsules or pellets may also contain water or other aqueous solutions to be time released so as to activate release of micro-organisms when oil transport (e.g.pipeline) occurs under arid (e.g. desert) conditions to aid remediation of a petroleum spill or discharge into a non-aqueous environment.

Preferably, such capsules, pellets, or pods contain micro-organisms, both aerobes and anaerobes or either of them.

In summary, this invention teaches: first, a methodology of preemption through the introduction of remediating agents into the petroleum product before a spill occurs; second, time or controlled release remediating agents encapsulated or pelletized as products of varying densities to provide for relatively even dispersal throughout the petroleum product; third, remediating agents which may include magnetic or similar materials, or means permitting the removal of unused remediating agents from a body of petroleum product which has not been subjected to aqueous environment; fourth, including anaerobes for the metabolism of submerged petroleum products, (which disperse throughout the petroleum bulk to exponentially increase the overall rate of bioremediation); and, fifth, time release of aqueous components within the product to effect remediation of spills into non-aqueous environments.

OBJECTS AND ADVANTAGES OF THE INVENTION

It is the object of the present invention to provide a pre-emptive bioremediation product of the character described for treating oil spills and discharge of petroleum based products.

Another object is to provide a method of the character described for pre-emptive remediation of oil spills and discharge of petroleum based products.

Another object is to provide a method for remediation of an oil spill which includes the step of installing a bioremediation agent into a contained body of petroleum before a spill or discharge occurs, the agent for bioremediation being activated upon contact with an aqueous environment.

Another object is to provide a method for remediation of an oil spill which includes the step of installing a time release aqueous solution into a pre-emptive bioremediation product so as to provide for remediation in the event of a spill or discharge into a non-aqueous environment.

Another object is to provide a method for remediation of an oil spill which includes the step of installing a time release aqueous solution into a pre-emptive bioremediation product so as to provide for remediation in the event of a spill or discharge which submerges below the water surface or sinks to the floor of the body of water.

Another object is to provide a pre-emptive method for remediation of an oil spill which includes the steps of fabricating a bioremediation agent for treating the spill with a component which facilitates easy removal of such agent when unused.

Another object is to provide timed and controlled release micro-organisms which are contained in products constructed of varying densities and sizes and which may be dispersed throughout a body of petroleum.

Another object is to provide a timed and controlled release micro-organism product which contains iron particulates, weighted or similar material or materials containing electrostatic or electro-conductive properties capable of use in separating such products from a body of petroleum by magnetic separation or similar techniques, or by centrifugation, precipitation, filtration, vaporization, heat or vacuum distillation, or a combination of these techniques.

Another object is to provide a timed and controlled release micro-organism product which contains ingredients for sustaining the micro-organisms before they are released into an petroleum spill or discharge.

Another object is to provide a timed and/or controlled release micro-organism product which contains catalytic ingredients for enhancing anaerobic bioremediation of an petroleum spill or discharge.

Another object is to provide a timed and/or controlled release micro-organism product which contains catalytic ingredients for enhancing aerobic bioremediation of an petroleum spill or discharge.

Another object is to provide a pre-emptive remediation method and micro-organism product for use in such a method which is efficient and economical.

These and other objects and advantages of the invention will become apparent as this description proceeds, taken in conjunction with the accompanying drawings.

BRIEF DESCRIPTION OF THE DRAWINGS

In the drawings:

FIG. 1 is a schematic view of a typical cell for the capsule, pellet, or pod embodying the present invention.

FIG. 2 is a sectional view of a typical pod of the bioremediation product containing multiple cells embodying the invention.

FIG. 3 is a diagram depicting the novel bioremediation products, comprising capsules, pellets, or pods arranged in a body of petroleum product.

FIG. 7 is a schematic view of the hold of a ship showing the release of bioremediation product with the escape of petroleum product during an oil spill.

FIG. 8 is a schematic view of a modified method for containing and release of bioremediation product with the escape of petroleum product during an oil spill, where the hold has a special liner for containing micro-organism product embodying the present invention which is activated upon penetration of the hold on contract with an aqueous solution at the time of a spill.

FIG. 9 is a schematic view of an oil spill floating in layers in a body of water, where the spill contains activated micro-organism product embodying the present invention.

DESCRIPTION OF PREFERRED EMBODIMENTS OF THE INVENTION

The Micro-Organism Pod

Figure 4:
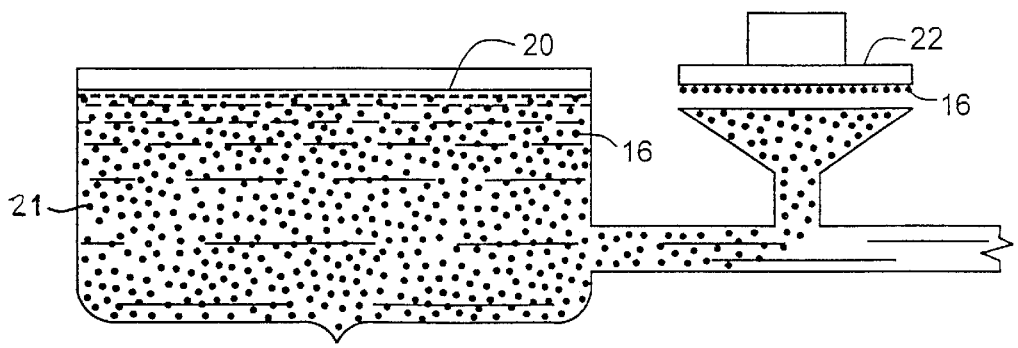
FIG. 4 is a schematic view of the hold of a ship filled with a body of petroleum containing micro-organism product, and illustrating a method including the use of magnetic means for removal of unspent product from the petroleum.

With reference to the accompanying drawings and particularly to FIGS. 1 and 2, a microcapsule cell 10 of anaerobic and aerobic micro-organism material having a micro-organism nucleus (N) 11 capable degrading a hydrocarbon, which may comprise bacterium which degrade petrochemicals, such as organisms from the genus vibrio, micrococcus, bacillus, arthrobacter, nocardis, corynebacterium and also including vibrio desulfuricans, Arthrobacter spp., *bacillus subtilis, B. licheniformis, B. megaterium, B. cereus, B. polymyxa, Aspergillus simplex, A. oryzae, A. niger, Trichoderma ressel,* Saccharomyces spp., Pseudomonas Mycobacteria, Achromobacter, *Geotrichum marinum,* Thirumalachar sp nov., or other hydrocarbon degradation bacterium. The nucleus 11 is preferably encapsulated by walls 12. The nucleus 11 may contain sufficient nutrients to sustain the micro-organism, however, the walls 12 separate the nucleus from a source of bacterium nutrients (B) 13 which facilitate growth and are presented to the bacterium in the presence of an aqueous solution which penetrates or dissolves the wall 12. As illustrated in FIG. 2, these and similar cells 10 may be enclosed in envelopes 14 which have a time released coating 15, such as hydrophilic methacrylate or gelatin to regulate the time of contact with the environment once exposed to water, and these coatings may be of varying thickness or density, which not only varies the time of release, but also varies the weight of the envelope.

Many such envelopes 14 may be enclosed in a pod or encapsulation 16, which may contain envelopes of varying weight and densities. Within such an encapsulation 16, in addition to the envelopes 14, may be a body of fluid 17, which may contain iron particulates or similar magnetic or paramagnetic particles 18. Such particles 18 may be useful not only in permitting easy recovery of unspent micro-organisms but also in providing synergistic material to enhance the effectiveness of the micro-organisms, as hereafter discussed. These pods 16 are preferably aqueous sensitive and may be breached when subjected to water, thus releasing the micro-organism for effective degradation of the hydrocarbon when a spill occurs.

The pod 16 as well as coating 12 may also contain time release aqueous solution to activate the petroleum consuming aerobic micro-organism when the spill is into a non-aqueous, oxygen available environment, as with an above ground pipeline spill (see FIG. 10), and activating as well anaerobic micro-organism for petroleum consumption when there is little or no oxygen about the spill, as when the pipeline is buried below ground (see FIG. 11). This also applies to the circumstance when the petroleum sinks below the water surface as may occur in a sea spill.

Loading Micro-organism Pods into a Body of Petroleum

Micro-organism pods 16 embodying the invention may be installed into a body of petroleum or hydrocarbon product 20 contained on a vessel or hold 21 at the wellhead, in a pipeline, during loading of the oil into a cargo hold, or at any other convenient location or time before an oil spill develops or discharge occurs. As illustrated in FIG. 3, pods 16 are spread through the body of petroleum product 20 contained in the hold 21 of a ship or in any other vessel used for oil during transport or storage. Installation of the pods 16 into the petroleum product 20 may be accomplished by convenient conventional means at any time during the transport or movement of the oil product from the well head until delivery for use, preferably before there is danger of an oil spill. For example, the micro-organism pods 16 may be aspirated into the body of petroleum 20 at the well head or into a pipeline or they may be contained in a quantity of fluid and pumped into the hold 21 of a ship.

Recovery of Unspent Micro-organism from Petroleum Product

As long as these pods 16 are not subjected to water or other means which will cause their content(s) to break into the environment of petroleum product 20, the pods remain latent and unspent and reusable once they are removed from the body of petroleum product 20.

These pods 16, if unspent, may be removed from the petroleum product 20 by several means. If the pods 16 contain iron filings or similar material 18, the pod 16 may be removed by magnetic separation when passed under a magnet 22 which draws the pods from the petroleum product 20, as illustrated schematically in FIG. 4.

Figure 5:
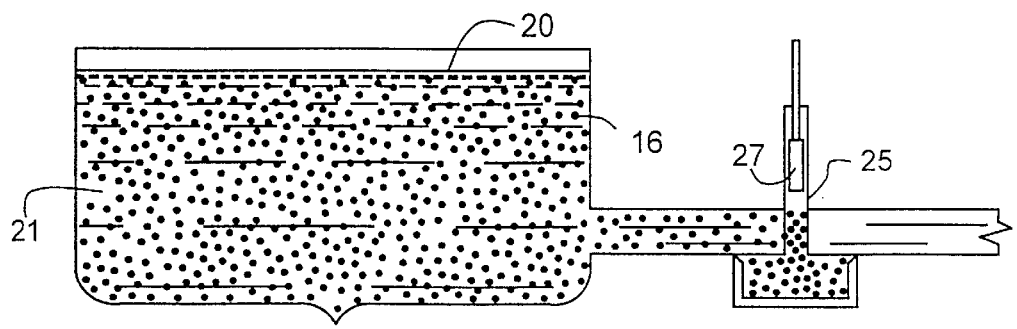
FIG. 5 is a schematic view of the hold of a ship like FIG. 4, but illustrating a modified recovery method including the use of filtration for removal of unspent product from the petroleum.

Another satisfactory means for removal of unspent pods 16 from the body of petroleum product 20 is by filtration, where a filter screen 25 or other barrier holds the pods and the petroleum fluid flows through the screen, induced to flow by gravity, pressure or suction. Means such as a blade 27 or a back wash may be used to remove the pods from the screen 25. Such a process for recovery of the pods 16 is schematically illustrated in FIG. 5.

Figure 6:
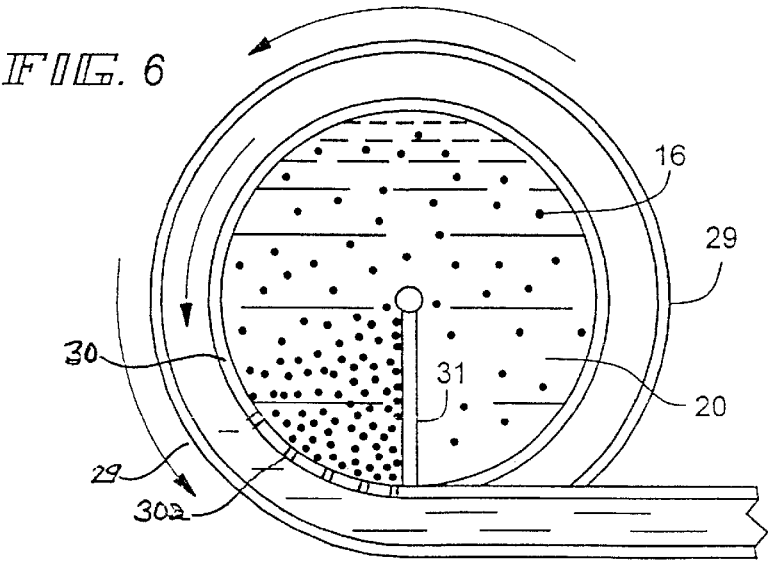
FIG. 6 is a schematic view of the another modified recovery method including the use of certrifugal action for removal of unspent product from the petroleum.

Alternatively, the pods 16 may be subjected to a centrifuge 29, as illustrated schematically in FIG. 6, where the centrifuge is spun and petroleum product 20 is separated from the pods which are accumulated on the inner wall 30 of the centrifuge for removal by a doctor blade 31 or similar means, as schematically illustrated in FIG. 6, thus allowing the fluid oil product 20 to be discharged through the screen 30a in the inner wall 30.

Other means may also be used for removal of the unspent pods 16 from the body of oil product 20, such as precipitation, vaporization, heat or vacuum distillation, or electrostatic processes and other fluid-solid separation means, which may or may not require special fabrication of the pods 16. The pods 16 may vary in size, weight, thickness, content and kinds of coatings to facilitate removal of unspent micro-organism from a body of petroleum.

Release of the Pods into a Aqueous Environment

With reference to FIG. 7, when a breach 32 of the hold 21 or vessel containing the oil product 20 occurs, the leaking of oil product through the breach in the vessel carries with it the pods 16, which when subject to water, become activated. The enteric coating 15 may be removed by the water or by time, and the micro-organism will be induced to consume the escaped petroleum product 33, and such consumption may be enhanced by the nutrients 13 packed with micro-organism, or these material may be used primarily to keep the micro-organism hearty over time before they are activated by the presence of water. A venturi-like effect carries the pods 16 into the spill, dispersing the micro-organism pods 16 throughout the escaped oil product 33 floating and submerged in contaminated water 34, as illustrated in FIG. 8, to consume the spilled oil product, as illustrated in FIG. 9.

A modified means for containing the micro-organism pods 16 is illustrated in FIG. 8, where the hold 21 has a double wall liner 35 into which the pods are placed separate from the body of oil product 20. In this way, the micro-organism pods 16 may or may not be mixed with the oil product 20 but are not released beyond their liner 35 until and unless there is a breach 32 through the hold and liner releasing escaped oil product 33 which pushes the pods into the body of contaminated water 34, wherein the micro-organism are activated for feeding, as described. Such a modified hold liner 35 arrangement not only reinforces the structure of the petroleum containing vessel 21, but also makes it easier to insert and withdraw unspent micro-organism pods 16, which may be gravity drained or pumped from the reservoir 36 within the double wall liner 35, or the liner may be removed.

Figure 10:
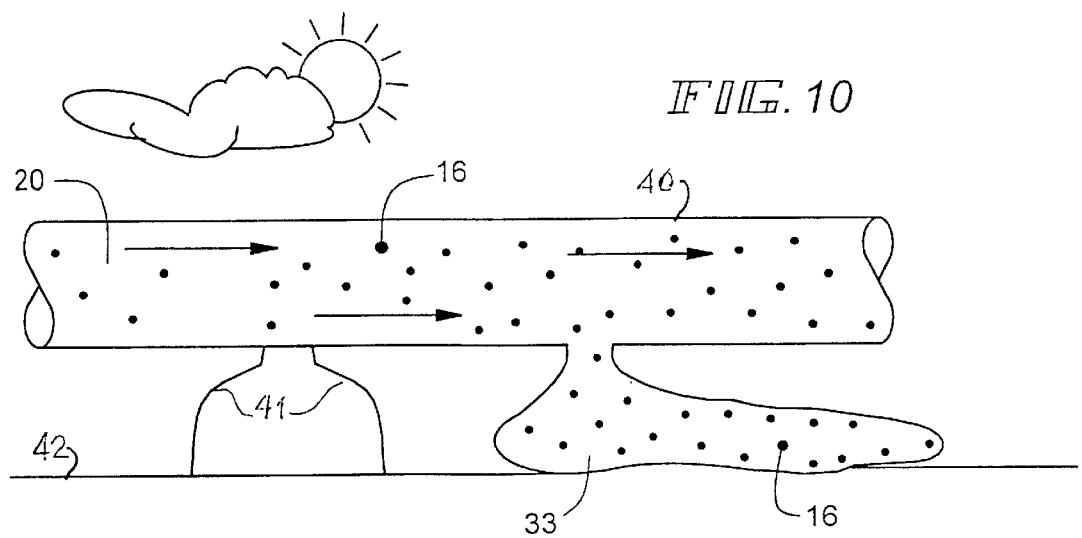
FIG. 10 is a schematic view of a pipeline elevated above ground where petroleum product spills into a non-aqueous aerobic environment and where time release aqueous materials activate microbial activity to consume the hydrocarbons.
Figure 11:
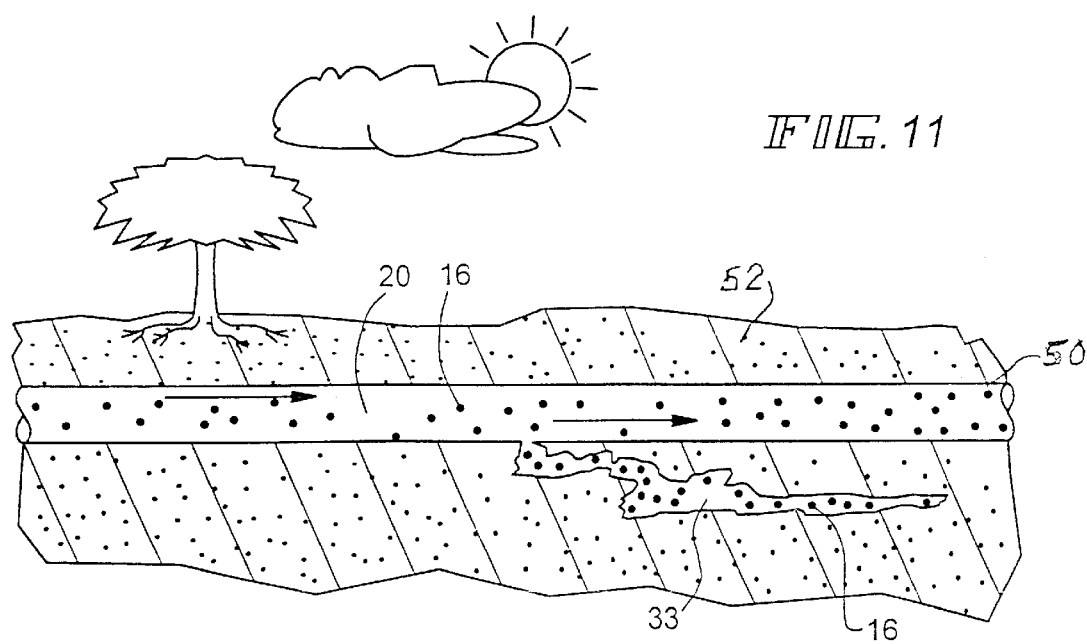
FIG. 11 is a schematic view of a petroleum discharge from a buried pipeline in a non-aqueous anaerobic environment where time release aqueous material activate microbial activity to consume the hydrocarbons.

As illustrated in FIG. 10, the vessel containing petroleum product 20 and these novel pods 16 comprises a pipeline 40 which is suitably elevated by supports 41 above grade 42, and the oil product admixed with the novel pods suitably containing aerobic micro-organism activated on exposure to a non-aqueous environment will consume spilled oil product 33 when a breach in the pipeline occurs and oil is unintentionally discharged. In FIG. 11, the vessel comprises a buried pipeline 50 which is installed below grade 52, and the admixed oil product and pods 16 suitably containing anaerobic micro-organism activated on exposure to a below grade environment will consumed spilled oil product 33 when a breach in such a buried pipeline occurs.

While preferred embodiments of the invention have been disclosed in considerable detail, many variations and changes in the method and micro-organism products described without departing from the spirit or scope of the invention. It is not desired that the invention should be limited to the exact structure and steps or order of steps disclosed, except as limited by the appended claims.

I claim:

1. A micro-organism pod for pre-emptive bioremediation of an oil spill escaped from a vessel containing a body of fluid petroleum product by using micro-organism capable of degrading such oil spill and for recovery of such micro-organisms from said vessel if unused to degrade such oil spill, said pod comprising micro-organism cell means capable of degrading hydrocarbons when exposed to a body of water, encapsulation means preventing exposure of said micro-organism cell means to said petroleum body until and unless said petroleum body spills from said vessel, and activation means adapted to release micro-organism into said petroleum body when said petroleum body spills from said vessel into said body of water, said pod having an initial specific gravity approximate the density of said petroleum product.

2. The pod recited in claim 1, with the addition of recovery means adaptable to remove unused micro-organism cell means from said petroleum body.

3. The pod recited in claim 1, wherein said micro-organism cell means contains a nucleus of anaerobic and aerobic micro-organism capable of degrading hydrocarbons.

4. The pod recited in claim 3, wherein said micro-organism cell means contains nutrients for said micro-organism.

5. The pod recited in claim 3, wherein a wall separates said micro-organism cell means from said encapsulation means.

6. The pod recited in claim 1, wherein said encapsulation means comprises an envelope containing said micro-organism cell means.

7. The pod recited in claim 6, wherein said encapsulation means has a time released coating.

8. The pod recited in claim 6, wherein said encapsulation means dissolves when exposed to water.

9. The pod recited in claim 6, wherein multiple envelopes are contained in said encapsulation means.

10. The pod recited in claim 9, wherein said envelopes vary in weight.

11. The pod recited in claim 9, wherein said envelopes vary in density.

12. The pod recited in claim 9, wherein said envelopes contain a body of fluid.

13. The pod recited in claim 6, wherein said encapsulation means contains magnetic material.

14. The pod recited in claim 1, wherein said activation means releases micro-organism discharged into an aqueous environment when said pod is exposed to water.

15. A micro-organism pod for pre-emptive bio remediation of an oil spill escaped from a vessel arranged in a defined environment comprising a first medium, said vessel containing a body of fluid petroleum product, and such bio remediation resulting from use of micro-organism in said pod capable of degrading such oil spill, said pod comprising micro-organism cell means containing bacteria capable of degrading hydrocarbons only when released into such defined environment, encapsulation means into which said cell means are placed preventing exposure of said micro-organism cell means to said petroleum body until and unless said petroleum body spills from said vessel into said first medium, and activation means adapted to release micro-organism into said petroleum body when said petroleum body spills from said vessel into said defined environment and said encapsulation means enters said first medium, said pod having an initial specific gravity approximate the density of said petroleum product.

16. The pod recited in claim 15, wherein said pod is carried with said petroleum product if said petroleum product spills from said vessel.

17. The pod recited in claim 15, wherein said pod has an enteric coating which may be removed by said first medium.

18. The pod recited in claim 15, wherein said pod is inacive except when exposed to said first medium.

* * * * *